United States Patent [19]

Sifniades et al.

[11] 3,941,776

[45] Mar. 2, 1976

[54] RESOLUTION/RACEMIZATION OF AMINOLACTAM COMPOUNDS

[75] Inventors: Stylianos Sifniades, Madison; William J. Boyle, Jr., Morristown; Jan F. Van Peppen, Chester, all of N.J.

[73] Assignee: Allied Chemical Corporation, New York, N.Y.

[22] Filed: July 1, 1974

[21] Appl. No.: 484,529

[52] U.S. Cl. 260/239.3 R; 260/326.45; 260/439 CY; 260/534 L; 260/561 A
[51] Int. Cl.² ............... C07D 223/10; C07D 223/12
[58] Field of Search ............ 260/239.3 R, 326.5 FL, 260/293.86

[56] References Cited
UNITED STATES PATENTS

| | | | |
|---|---|---|---|
| 3,024,231 | 3/1962 | Scherrer | 260/239.3 R |
| 3,105,067 | 9/1963 | Nelemans et al. | 260/239.3 R |
| 3,275,619 | 9/1966 | Brenner et al. | 260/234.3 R |
| 3,542,766 | 11/1970 | Ohnogi et al. | 260/239.3 R |
| 3,591,579 | 7/1971 | Shibahara et al. | 260/239.3 R |
| 3,658,811 | 4/1972 | Tanaka et al. | 260/239.3 R |
| 3,692,775 | 9/1972 | Kubanek et al. | 260/239.3 R |
| 3,824,231 | 7/1974 | Kubanek et al. | 260/239.3 R |
| 3,842,073 | 10/1974 | Fuhrmann et al. | 260/239.3 R |

*Primary Examiner*—John D. Randolph
*Assistant Examiner*—Robert T. Bond
*Attorney, Agent, or Firm*—Arthur J. Plantamura

[57] ABSTRACT

Resolution of α-amino-ε-caprolactam with simultaneous racemization of the undesired α-aminocaprolactam enantiomer is effected by preferentially crystallizing the L- (or D-) α-amino-caprolactam compound in the presence of a racemization catalyst. In a narrower embodiment racemization of α-amino-ε-caprolactam is effected by alternate routes of forming a coordinately saturated aminolactam-metal complex and reacting with a strong base or reacting a mixture of an aminolactam salt and aminolactam free base with a chelating carbonyl compound and a metal ion or reacting a mixture of an aminolactam salt and aminolactam free base in the presence of a salen derivative complex.

21 Claims, 1 Drawing Figure

U.S. Patent   March 2, 1976   3,941,776
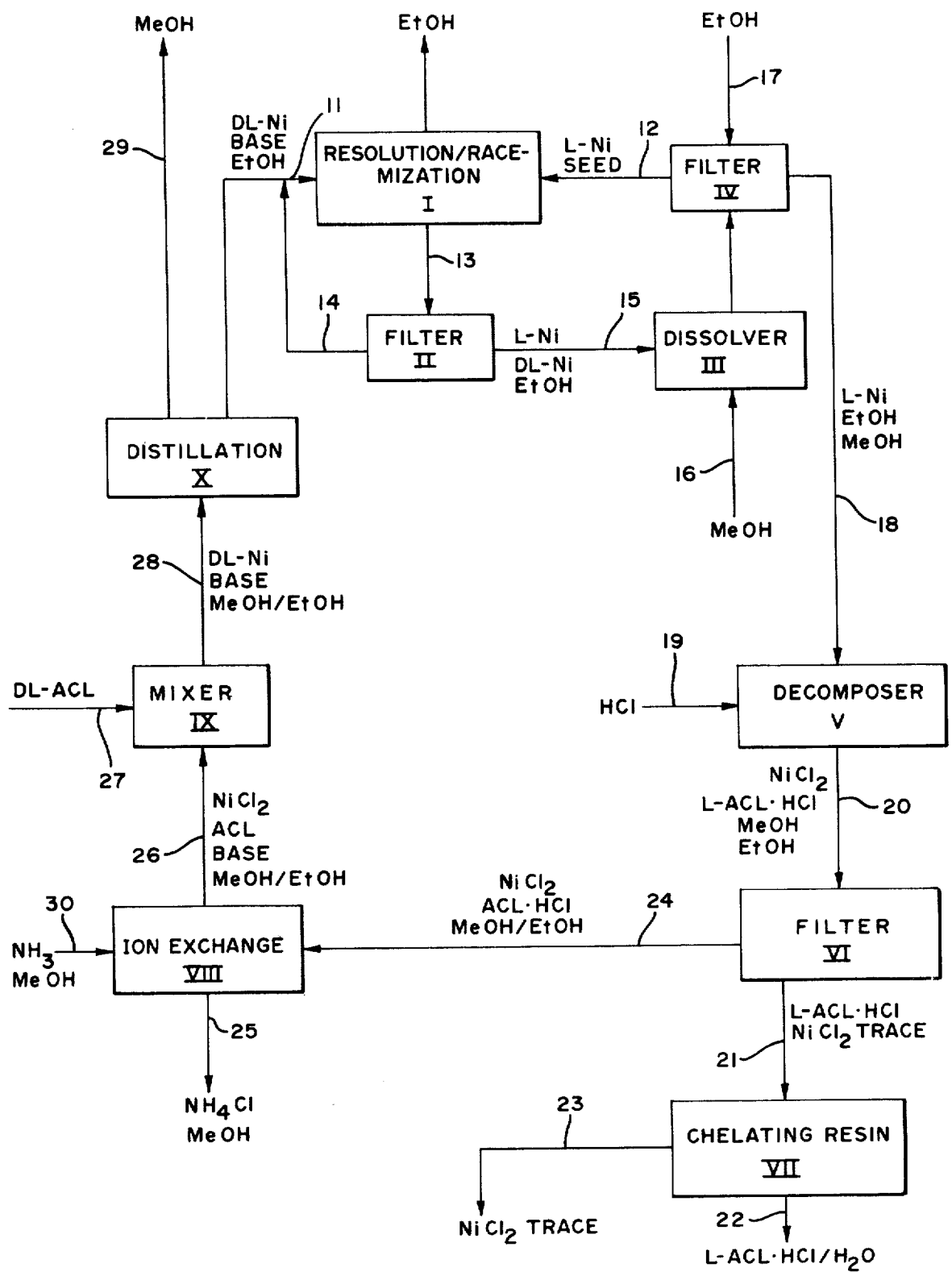

RESOLUTION/RACEMIZATION OF AMINOLACTAM COMPOUNDS

BACKGROUND OF THE INVENTION

1. Field of the Invention

The invention in a preferred embodiment relates to a simultaneous, one-stage resolution/racemization procedure for α-amino-ε-caprolactam. This invention relates also to a novel method for the racemization of optically active α-amino-ε-caprolactam at relatively low temperatures.

2. Brief Description of the Prior Art

Often one enantiomer of a compound having D- and L-forms is preferred over the other enantiomer of that compound. For example, lysine, an essential amino acid, exists in both D- and L-forms; however, only L-lysine possesses nutritional value. Although many synthetic methods for the production of lysine have been proposed, all non-biological methods have entailed preparation of either D,L-lysine or a D,L-racemic mixture of a lysine precursor such as D,L-lysine amide or D,L-amino-ε-caprolactam. If used in this racemic form, these precursors would lead to the production of D,L-lysine or salt thereof. Such a mixture might conceivably be used without separation of the non-nutritional D-isomer but such a procedure would result in considerable waste. It is therefore advantageous to separate or resolve the two enantiomers to recover the desired enantiomer and then to racemize the non-nutritional or useless D-enantiomer to form additional D,L-racemic mixture from which the desired L-enantiomer is again recovered, with the procedure being repeated as often as desired. In accordance with a procedure of this kind, essentially all the D-enantiomer is in course transformed into the desired L-form. Similarly for other compounds in which the D-, rather than the L-, enantiomer is desired, this procedure allows racemization of the L-enantiomer to yield additional D-enantiomer and subsequent recovery of the D-form.

Although methods are known to effect resolution and racemization of α-amino-ε-caprolactam as separate operations, no procedure is known which accomplishes both resolution and racemization in a single stage operation. An example illustrating resolution is the procedure disclosed in U.S. application Ser. No. 301,409, entitled "Resolution of α-aminocaprolactam", filed Oct. 27, 1972, now U.S. Pat. No. 3,824,231, wherein racemic mixture of D,L-α-aminocaprolactam are resolved in accordance with a method comprising:

a. forming a complex by admixing D,L-α-amino-ε-caprolactam at about 10°–100°C. in a solvent such as methanol, ethanol or isopropanol, or mixtures thereof, with metal ions, e.g. nickel in the plus 2 valence state;

b. separating a solid phase rich in the D- or L-isomer by seeding the solution with crystals of an aminocaprolactam metal complex of the respective D- or L-isomer;

c. recovering L-α-aminolactam from the precipitated L-isomer complex;

d. racemizing the precipitated D-isomer complex and recycling to step (b).

Racemization of optically active α-amino-ε-caprolactam in the presence of $Ni^{++}$ and other transition metal ions is disclosed also in U.S. Pat. No. 3,692,775.

It is also known that the racemization of optically-active aminolactams and amides of amino acids can be carried out in the presence of sodium by distillation in the absence of a solvent under vacuum at elevated temperatures, e.g. 180° to 190°C. This process has the disadvantage that high temperatures must be employed and only about 70% recovery is obtainable; these conditions add substantially to the expense of such process. Another process wherein racemization of aminolactams occurs by sodium hydroxide treatment in the presence of organic solvents, such as toluene and other hydrocarbons, is disclosed in U.S. Pat. No. 3,105,067. This process has the disadvantage that the comparatively high boiling point of the solvent makes it difficult to obtain a solvent-free product and adds to the heat requirements needed to recover the solvent for recycle. These conditions, moreover, add substantially to the capital investment and the operating costs of such process.

Because crystallization of the desired enantiomer occurs only from a supersaturated solution of the enantiomer to be recovered, only a small fraction of the desired enantiomer can be recovered in one crystallization stage before the supersaturation is depleted. The extent of crystallization may be increased by simultaneously removing solvent, e.g. by evaporation. In that case, however, the concentration of the undesired enantiomer would increase and eventually it would also crystallize out, thus disrupting the resolution. It is, therefore, necessary to keep the extent of crystallization, i.e. resolution, at a relatively low level. The remaining solution consists of the rest of the desired enantiomer and the undesired enantiomer. Since previously known racemization techniques require the application of elevated temperatures which produces significant losses of the desired enantiomer, it has heretofore been undesirable, therefore, to racemize the entire mother liquor remaining after one crystallization step because of the irretrievable thermal loss of the desired enantiomer in the racemization process. For this reason a method has been employed which entails passing the D,L-α-aminocaprolactam/metal complex solution over alternate beds of D- and L-seed crystals. After contacting a solution of either isomer with a D- or L-seed bed and depositing part of the D- or L-isomer, the liquor is re-enriched by dissolving additional D,L-α-aminocaprolactam metal complex, e.g. by heating at a higher temperature, and/or part of the solvent evaporated off to concentrate the solution and thereby facilitate further precipitation of the other isomer; the solution is then passed to a seed bed of the other isomer, which isomer is preferentially precipitated. After passing over the alternate isomer seed beds with concentration or enrichment after each precipitation, the solution will contain approximately equivalent concentrations of both isomers. New D,L-mixture is continuously added to the recycling process stream, with D- and L-isomer crystals being separately deposited from the solution onto the beds. After recovery, the undesired D-crystals are then dissolved, racemized and recycled while the desired L-crystals are separated from the metal complex and further treated.

If a method could be provided which effects racemization of α-amino-ε-caprolactam at relatively low temperatures and with substantially no loss of α-amino-ε-caprolactam, it would be advantageous because it would permit racemization of the entire mother liquor remaining after recovery of the desired α-amino-ε- caprolactam enantiomer; thus greatly simplifying the resolution/racemization process.

A still greater simplification would result, however, if it could be demonstrated that racemization of the undesired α-amino-ε-caprolactam enantiomer could take place simultaneously with the resolution of the desired enantiomer. In this case, the resolution/racemization process would take place in a single stage, thus eliminating the need for a separate racemization reactor. Moreover, since the undesired enantiomer would be continuously transformed to the desired enantiomer by means of racemization, it would become possible to effect high recovery of the desired enantiomer in a single pass without danger of crystallizing at the same time as the undesired enantiomer.

There is thus a need for a method in which resolution of racemic compounds may be effected simultaneously with racemization of the undesired optical isomer so as to effect a single stage operation.

There is also a need for a racemization method which may be effected at relatively low temperatures thereby allowing racemization of a mixture containing both the desired and undesired enantiomers without suffering a loss of the desired enantiomer.

SUMMARY OF THE INVENTION

In accordance with the present invention, α-amino-ε-caprolactam (ACL) may be rapidly and effectively resolved and racemized in a single operation instead of by the multiple stage procedures required heretofore. In practicing the invention, the resolution of α-amino-ε-caprolactam and racemization of the undesired aminocaprolactam enantiomer may be effected in a single stage in a convenient and expeditious manner. We have discovered that solutions of aminocaprolactam complexes or salts can be rapidly racemized, as described hereafter, at relatively low temperatures. Crystals of optically active aminocaprolactam complexes or salts of aminocaprolactam do not significantly racemize when suspended in a medium containing the dissolved complex or salt under the conditions that effect racemization in solution. We have further discovered that optically active crystals suspended in a supersaturated solution of the corresponding racemic compound effect resolution by preferential crystallization of one isomer even under conditions of relatively fast racemization in the solution. Further, we have found that we can effect resolution of α-amino-ε-caprolactam by making a diastereomeric salt with an optically active acid and preferentially crystallizing the diastereomeric salt of L-α-aminocaprolactam with simultaneous racemization of the D-α-aminocaprolactam; under these conditions, the optically active acid does not significantly racemize. The steps in the combined resolution/racemization of D,L-aminocaprolactam comprise:

a. forming a supersaturated feed solution of an aminocaprolactam compound and maintaining said solution at a temperature of below 120°C. and under conditions such that the racemization rate constant of aminocaprolactam is at least 0.001 min.$^{-1}$;

b. contacting said solution with seed crystals of the desired isomer of said compound; and c. removing the grown crystals of said compound.

In a preferred embodiment crystallization of a complex salt of the desired enantiomer of ACL is effected using seed crystals of the complex of the same enantiomeric structure. Two such suitable complex salts are $(ACL)_3NiCl_2$ and $(ACL)_3CoCl_2$.

To effect the single stage resolution/racemization, the resolution procedure disclosed above in connection with copending application Ser. No. 301,409, now U.S. Pat. No. 3,824,231, may be adapted with the important modifications which follow.

The single stage process, according to the present invention, may be conducted due to the fact that ACL complexed with $Ni^{++}$ can be easily racemized, provided that a strong base is present and provided further that excess ACL is present, at the same temperature that resolution takes place. When so conducted, the desired enantiomer [e.g. $(L-ACL)_3NiCl_2$] is resolved by crystal growth on seed crystals of this enantiomer, while the undesired enantiomer [e.g $(D-ACL)_3NiCl_2$] simultaneously racemizes in solution. The steps employed to effect this single stage process in essence involve the same above-noted steps of (a) forming the complex of α-aminocaprolactam and (b) separating a solid phase rich in the D- or L-isomer. However, the procedure is modified by the following considerations:

In step (b) when contacting said supersaturated solution with seed crystals of the corresponding complex salt of the desired enantiomer, a strong base catalyst and ACL-free base are employed in combination with an appropriate temperature so that the rate of racemization in solution is relatively fast.

It is thus seen that a relatively expeditious and convenient single-operation resolution/racemization is expected. In particular, no separate steps are necessary to recover and racemize the undesired enantiomer.

As an alternate procedure which combines resolution and racemization a method which involves the preferential crystallization of a salt of the desired enantiomer of ACL on seed crystals of the salt of the same enantiomeric structure is used. Illustrative salts which may be so resolved into two enantiomeric forms are ACL.HCl, ACL.HBr, ACL.β-naphthalene sulfonic acid, ACL.2-naphthylamine sulfonic acid, and the like.

The steps required to effect resolution in this alternate procedure are similar to steps (a) and (b) described in the case of the resolution of complex, except that a salt is substituted for the complex of the hereinabove described process.

In using salts in the latter process it is somewhat more difficult to transform the resolution/racemization into a single stage process because of the increased difficulty of racemization of the salt at temperataures low enough to effect resolution. We have discovered the following mechanism which offsets this difficulty.

Free ACL is mixed with the salt and at the same time a catalyst which racemizes ACL is introduced. Since exchange between free ACL and ACL salt is rapid in solution, racemization of ACL results in racemization of the ACL salt also. The following precautions of a practical nature should be adhered to:

The catalyst should remain in solution while the L-ACL salt crystallizes; this normally requires the use of dilute concentrations of catalyst.

At low catalyst levels the racemization is slow at the temperatures at which resolution has been disclosed in the prior art. Illustrative of such prior art are the following:

U.S. Pat. No. 3,591,579 involving resolution of ACL salts with β-naphthalene sulfonic acid or 2-naphthylamine-1-sulfonic acid disclosing a temperature of 20°–30°C., or Belgian Pat. No. 788,009, Dec. 18, 1972, involving resolution of DL-ACL.HCl in presence of DL-ACL at a temperature of 20°–45°C.

In accordance with the purposes of the present invention, therefore, we have found that operation at temperatures higher than 45°C. is desirable in order to have a sufficiently high racemization rate.

At increased temperatures, however, the adverse effect of temperature on resolution must be considered. Therefore, the lowest temperature consistent with suitable racemization and as determined by the catalyst utilized should be employed. It is to be noted that the fact that resolution could be effected suitably at higher temperatures itself is not obvious from the prior art.

Illustrative catalysts which may be used for racemization of the salt/ACL mixtures are the following:

A. Derivatives of chelating carbonyl compounds such as salicylaldehyde, e.g. 5-nitrosalicylaldehyde and metal ions, e.g. $Fe^{2+}$, $Fe^{3+}$, $Al^{3+}$, $Cu^{2+}$, $Ni^{2+}$ and the like.

B. Complexes of salen derivatives with $Fe^{++}$ or $Co^{++}$, e.g. $Fe^{II}$ (5-nitrosalen), shown in the following formula:

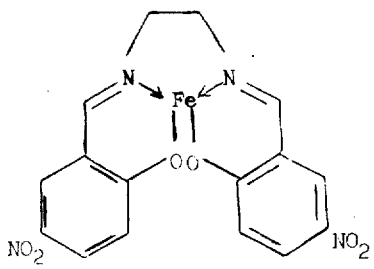

Still another alternative method of effecting a single stage resolution/racemization involves the preferential crystallization of a diastereomer salt of the desired enantiomer of ACL. Illustrative of diastereomeric salts is the disclosure in U.S. Pat. No. 3,275,619 relating to resolution of ACL with 2-pyrrolidone carboxylic acid. In this embodiment, use of seed crystals of the same diastereomeric structure is optional since once the process is started the crystals once formed inherently are present in the system.

Several such diastereomeric salts are known which may be utilized including the following:

L-ACL.L-pyrrolidone carboxylic acid
L-ACL.D-N-carbamoyl valine
L-ACL.L-N-p-nitrobenzoyl glutamic acid
L-ACL.L-N-benzoyl glutamic acid
L-ACL.L-N-p-toluyl glutamic acid
L-ACL.L-N-p-chlorobenzoyl glutamic acid and the like. In general, the steps employed in this type of resolution comprise:

a. forming diasteromeric salts of ACL by reaction with one enantiomer form of an asymmetric acid in a suitable solvent,
b. crystallizing preferentially the diasteromeric salt of the desired enantiomer of ACL and separating said preferred salt. Subsequently, steps are taken to recover the undesired enantiomer of α-aminocaprolactam, to racemize said enantiomer and to recycle same to step (a). In accordance with the invention, the crystallization of the diasteromeric salt of the desired aminolactam enantiomer can be effected under conditions such that racemization in solution of the undesired aminolactam enantiomer is relatively fast permitting a single stage resolution/racemization.

The catalyst systems utilized may include those described hereinabove with reference to the system utilizing an enantiomeric salt. The considerations outlined in connection with the above alternative relating to the use of dilute concentration of catalysts apply also in general in this embodiment. Moreover, in connection with use of diasteromeric salts the optically active acid used to form the L-ACL diastereomeric salt must not racemize substantially under the conditions of ACL racemization/resolution.

While we do not wish to be limited thereby, the following theory is submitted as applicable to the system of the invention wherein resolution of one enantiomer (i.e. the L) with simultaneous racemization of the other enantiomer (i.e. the D) occurs. In the system at steady state, i.e. when the rate of resolution is equal to the rate of racemization, it is postulated that:

Rate of Resolution = $k_r(C_D - C_L)$ where $C_D$ is the concentration of the D-enantiomer and $C_L$ the concentration of the (desired) L-enantiomer and $k_r$ is the rate constant of racemization which must be at least 0.001 min.$^{-1}$. More generally, a range of from about 0.01 min.$^{-1}$ to about 10 min.$^{-1}$ is contemplated. From this equation, at steady state the rate of resolution is proportional to the rate constant of racemization and to the excess concentration of D- over L- in solution. The excess of D- over L- in solution cannot exceed a certain limit, e.g. $C_D$ 2$C_L$, without causing crystallization of the D-species which would disrupt the resolution process. Thus, for a simultaneous combined resolution/racemization process, the parameter of prime importance is the rate constant of racemization, $k_r$. The value of $k_r$ can be increased in either of two methods: first, it may be increased by raising the reaction temperature since, in general, the rate constants approximately double for every 10°C. rise in temperature. However, a rise in temperature will also increase the solubility of the species to be resolved and may also cause undesirable side reactions. Another way to increase the rate constant $k_r$ is to utilize a suitable catalytic system. A catalyst system which we have found to be suitable in the case of ACL complex resolution/racemization comprises a combination of a metal complex of ACL and a strong base under conditions of coordinational saturation of the metal ion. Using this system we are able to increase $k_r$ by a factor in the order of 1000 and even more at a given temperature. In contrast, to obtain a comparable increase in $k_r$ using conventional racemization methods, it would be necessary to raise the reaction temperature about 100°C. to a temperature at which it would be difficult to effect resolution or at least economically and technically not feasible. In the case of resolution/racemization of ACL enantiomeric salts and ACL diastereomeric salts, the catalyst systems which are best suited comprise a combination of the ACL (enantiomeric or diastereomeric) salt, ACL-free base, and either a derivative of a chelating carbonyl compound, e.g. salicylaldehyde in the presence of metal ions, e.g. $Fe^{2+}$, $Fe^{3+}$, $Al^{3+}$, $Cu^{2+}$, $Ni^{2+}$ and the like, or a $Fe^{2+}$ or $Co^{2+}$ complex of salen or of a derivative of salen.

While the preferred objective of the present invention involves a process for simultaneous resolution and racemization, the invention contemplates also a novel racemization method per se. Racemization of aminocaprolactam in the prior art was effected at relatively high temperatures and relatively long periods, e.g. temperatures of the order of 100°C. and about 4 hours, whereas the present invention may effect essentially complete racemization at substantially lower temperatures, i.e. below about 80°C. and in periods of time of the order of 30 minutes.

Moreover, in conjunction with the enantiomeric salt and diastereomeric salt systems of the present invention, it is found that such systems are compatible with aminolactam salts whereas with known systems of the prior art generally a strong base would interact with lactam salts resulting in decomposition to free aminolactam and formation of an inorganic salt.

It is thus seen that in some instances by using the racemization procedures described by the present invention, it may be advantageous to conduct the racemization and resolution in separate stages. In particular, when the resolution cannot be conducted efficiently at temperatures of efficient racemization, e.g. aminolactam β-naphthalenesulfonate resolves very efficiently at about 30°C., whereas at higher temperatures, i.e. where the rate of racemization is higher, the efficiency of resolution is relatively low. In this case it would clearly be advantageous to effect racemization at about 65°C. and the resolution in a separate stage at about 30°C.

BRIEF DESCRIPTION OF THE DRAWING

The flowsheet is illustrative of a continuous single stage process in which the aminocaprolactam-nickel chloride complex is racemized and resolved according to a preferred embodiment of the invention.

DESCRIPTION OF THE PREFERRED EMBODIMENTS

In effecting the single stage racemization/resolution utilizing a metal complex and amino-ε-caprolactam, the metals whose ions may be employed, include nickel and cobalt or mixtures of these ions in the plus 2 valence state. The mol ratio of α-amino-ε-caprolactam to metal ion ranges from a minimum of about 3:1 to about 20:1, preferably from about 3.5:1 to about 10:1.

The particular salt of the metal is chosen so that it is soluble in a suitable organic medium to the extent necessary to provide the desired ion/aminocaprolactam ratio. Any of a variety of salts of the Ni and cobalt ions in the plus 2 valence state may be employed in the racemization of the α-amino-ε-caprolactam, e.g. salts of mineral acids and organic acids, such as chlorides and the other halogens; sulfates; nitrates; phosphates; acetates; benzoates; and the like. The chloride salts are preferred.

In the single stage resolution/racemization the complex which is formed, it will be apparent, must also be capable of resolving. While a variety of nickel and cobalt salts may also be used in forming the complex with a α-amino-ε-caprolactam to effect resolution, nickel chloride or cobalt chloride are preferred.

The α-amino-ε-caprolactam and metal ion may be contacted with each other by various conventional methods, preferably by dissolving salts of the above-defined metals in an α-amino-ε-caprolactam containing medium such as an aminocaprolactam melt or solution, preferably the latter.

In order to effect rapid racemization the presence of a strong base is necessary. The function of the strong base is to facilitate elimination of the α-proton of complexed α-aminocaprolactam which results in racemization. It is essential, also, to the process of the present invention that the metal ion complex be coordinately saturated, i.e. so that the strong base cannot coordinate to a large extent with the metal ion. To the extent that such coordination takes place, the strong base does not function as a catalyst. The preferred method for insuring that the ion is coordinately saturated is to employ an excess amount (i.e. more than 3 moles per mole metal ion) of α-amino-ε-caprolactam which will chelate with any available coordination sites on the α-amino-ε-caprolactam metal ion complex. Alternatively, the α-amino-ε-caprolactam metal ion ratio may be maintained at 3:1 and another complexing agent, e.g. ethylene diamine, sodium lysinate, 1,10-phenanthroline ammonia and the like, may be employed.

Any solvent which will dissolve both the metal salt and α-amino-ε-caprolactam without substantial reaction is suitable.

Suitable solvents for the preparation of ACL complex solutions include alcohols which dissolve greater than 2 volume percent water at 20°C., including, for example, alcohols such as methanol, ethanol, isopropanol, allyl alcohol, ethylene glycol, diethylene glycol, glycerol, and 2-methoxyethanol. Preferably the solvent is methanol, ethanol, isopropanol or a mixture thereof, containing less than about 5 volume percent water, especially ethanol, and including anhydrous alcohols. Solvents containing greater than about 5% water should be avoided since hydrolysis of α-amino-ε-caprolactam to lysine may result. Also, the rate of racemization is depressed to some extent in the pressure of water.

Strong bases suitable for use in the invention include the alkali and alkaline earth metal salts and hydroxides thereof, such as potassium hydroxide, sodium hydroxide, and the like; carbonates such as sodium carbonate, calcium carbonate and the like; oxides, such as calcium oxide, magnesium oxide and the like; amides such as sodium amide, lithium amide and the like; alcoholates such as sodium ethoxide, potassium ethoside and the like; and quarternary ammonium compounds such as tetrabutylammonium hydroxide, tetraisopropylammonium hydroxide and the like, as well as strongly basic anion exchange resins such as those of the quarternary ammonium type. Particularly well suited bases are hydroxides or alkoxides of the metal ions of nickel and cobalt, which are used in the resolution/racemization reaction. Solutions of such hydroxides or alkoxides can be conveniently prepared by treating an alcoholic or aqueous alcohol solution of a salt of the metal ion with any of a variety of commercially available strongly basic ion exchange resin of the quaternary ammonium type, e.g. ANGA-542 or Amberlite IR 400 or a weakly basic ion exchange resin of tertiary amine type, e.g. Amberlite IR 45, Dowex 21K, etc. The amount of base employed is not critical; however, generally from about 1 to about 100 mol percent of the base may be used although preferably about 5 to about 30 mol percent is used based on the metal ion.

The racemization reaction of the instant invention can take place at any temperature between ambient temperature and the point at which said medium boils under the prevailing pressure conditions. Generally, the higher the temperature the faster the rate of racemization. The reaction is essentially unaffected by pressure and thus, for convenience, is preferably run at atmospheric or slightly above atmospheric pressure. With an α-aminocaprolactam solution in which racemization takes place simultaneously with resolution, a reaction temperature approaching the boiling point of the medium is usually preferred since the solvent liquor can be evaporated simultaneously with the resolution/racemization reaction. This method is particularly suited to a continuous operation in which α-aminocaprolactam complex solution and L-α-amincaprolactam complex seed crystals are continuously fed to a flow reactor while grown L-aminocaprolactam complex crystals are removed by filtration. The solvent is removed by evaporation. Excessive temperatures in some instances can cause adverse side reactions such as hydrolysis. The desired temperature range is generally from about 50° up to about 120°C. and preferably the temperature employed is in a range from about 70° to about 95°C.

The time required to effect total racemization, i.e. for the transformation of 100 percent D- or L-α-amino-ε-caprolactam into a 50/50 D,L-racemic mixture will vary but is readily determinable by one skilled in the art and will depend on the temperature of reaction and the concentrations of the starting material, chelating agent, base and catalyst. Under optimum conditions periods up to about 5 minutes to 1 hour will be adequate for complete racemization.

In the preferred embodiment of the present invention which comprises the one-stage resolution/racemization of α-amino-ε-caprolactam complex, the resolution and recrystallization of the desired enantiomer is achieved by contacting the solution with a seed bed of crystals of the metal complex of the desired enantiomer. The addition of the seed crystals will cause the desired enantiomer to preferentially crystallize out around the seed crystals leaving a solution rich in the undesired enantiomer to be racemized. The more concentrated the starting solution, the more readily crystallization occurs. However, we have found that solutions containing from about 10 to about 60 wt. % dissolved complex are most suitable for use in the instant process. It will be understood that the initial solution which is contacted with the seed crystals need not be exactly a 50/50 mixture of D- and L-isomers.

The term "seed bed" as used herein is well known in the crystallization art and connotes either a fixed or fluidized crystal bed or even a simple stirred vessel containing seed crystals.

The amount of seed crystals used to initiate crystallization from the solution can vary widely but ordinarily it is desirable to contact the solution with at least about 1.0 wt. % of seed crystals based on the weight of the mixture of isomers present in solution. Seed crystals are initially prepared by contacting optically pure L-aminocaprolactam (or D-aminocaprolactam) with the appropriate metal salt. In a continuous resolution/racemization process, seed crystals are obtained by subjecting to purification all or a portion of the crystalline product obtained in said process. Purification may consist of recrystallization or simply partial dissolution of the crude crystalline product.

To effectuate recovery of the desired product in its uncomplexed form, various conventional methods may be employed. A process which may be suitably used is one in which the metal complex which has crystallized out is dissolved or suspended in solvent, preferably a $C_1$ to $C_3$ alcohol, and treated with any strong non-oxidizing mineral acid, preferably hydrochloric, sulfuric or phosphoric. The acid effects decomposition of the complex and the simultaneous precipitation of the desired enantiomer of L-α-amino-ε-caprolactam as the acid salt. The decomposition can be effected at any temperature above about 0°C. This may conveniently be effected at ambient or slightly above ambient temperature.

The preferred acid for decomposition of the L-amino-ε-caprolactam metal complex is hydrochloric acid. As disclosed in U.S. Pat. No. 3,824,231, use of this acid provides the following advantage: Normally, the L-α-aminocaprolactam metal complex obtained in the present resolution/racemization process contains small but definite amounts of D,L-α-amino-ε-caprolactam metal complex. When the decomposition of the complex is effected by hydrochloric acid, the α-aminocaprolactam hydrochloride which crystallizes out is essentially optically pure, i.e. it is composed almost exclusively of L-α-amino-ε-caprolactam hydrochloride. The small amount of D,L-α-amino-ε-caprolactam hydrochloride, which is also produced during the decomposition, remains in solution.

Since the L-amino-ε-caprolactam is ordinarily further utilized in the form of its hydrochloride salt, this is the preferred form of this material. L-α-amino-ε-caprolactam hydrochloride can be hydrolyzed by known methods to afford L-lysine-hydrochloride salt.

A flowsheet illustrative of the continuous single stage resolution/racemization process is shown in the drawing. D,L-α-amino-ε-caprolactam nickel complex (represented in the drawing as DL-Ni) in ethanol originating in mixer IX and passing through column X is fed at 11 into resolver/racemizer I along with a strong base catalyst which originates in the ion exchanger VIII, although the main portion of the strong base catalyst for the racemization is provided by recycle stream 14 which is also introduced into reactor I. Nickel complex seed crystals of the desired L-α-amino-ε-caprolactam 12 are also introduced into reactor I. Ethanol is distilled and removed from reactor I. $(L-ACL)_3NiCl_2$ crystallizes out in the presence of $(L-ACL)_3NiCl_2$ seed crystals while racemization of D-ACL occurs simultaneously. The reaction mixture is continuously withdrawn at 13 and filtered at II with the mother liquor 14 being added to recycled stream 11. The L-α-amino-ε-caprolactam nickel complex filter cake which is withdrawn from filter II at 15 is transferred to dissolver III. In the dissolver III, the cake is refluxed with methanol, shown entering at 16; this results in partial dissolution of the crystals and optical upgrading of the residue. Optionally, the dissolver III may contain, or have attached thereto, means for reducing the size of the residual crystals. Such means include, for example, high speed stirring, ball milling, etc. The residual crystals are filtered and washed at IV with ethanol shown entering at 17 and the purified metal complex crystals are added as seed 12 to the resolution/racemization reactor I. The filtrate is passed in stream 18 to decomposer V where anhydrous HCl shown entering at 19 is introduced to effect decomposition of the metal complex. The contact with HCl decomposes the L-α-ACL.NI complex and precipitates optically pure L-α-ACL.HCl. Any lysine which may be present as impurity also crystallizes as lysine.HCl. The resulting stream 20 is filtered at VI and the crystalline L-ACL.HCl containing traces of $NiCl_2$ is redissolved in water (not shown) and passed at 21 through a chelating resin at VII where the optically pure L-ACL.HCl is separated at 22 from the $NiCl_2$ traces 23 which is recovered or may be recycled (now shown). The purified aqueous L-ACL.HCl may be further hydrolyzed to L-lysine.HCl by reaction with hydrochloric acid. The mother liquor removed at 24 comprises dissolved $NiCl_2$, a small amount of dissolved, D,L-α-ACL.HCl and alcohol solvent. This mother liquor is neutralized by contacting with a basic ion exchange resin in column VIII where the D,L-α-ACL.HCl is neutralized to the free base D,L-α-ACL and part of the $NiCl_2$ is transformed to basic nickel chloride. The resin is regenerated to its basic form by a methanol solution of ammonia introduced at 30 which removes the chloride ions as a methanol solution of $NH_4Cl$, as shown at 25. The remaining alcohol solution of ACL, $NiCl_2$, and basic nickel chloride via 26 is combined in a mixer IX with feed, D,L-ACL introduced at 27 to form a solution of D,L-α-aminocaprolactam nickel complex and strong base catalyst. The thus produced solution introduced via line 28 is distilled at X to remove methanol as shown at 29; the remaining stream 11 is recycled to I.

An alternate procedure which combines resolution and racemization and which involves the preferential crystallization of a salt of the desired enantiometer of ACL on seed crystals of the salt of the same enantiomeric structure may be used. Illustrative salts which may be utilized in this alternate procedure are ACL.HCl, ACL.HBr, ACL.β-naphthalenesulfonic acid, and ACL.2-naphthylamine sulfonic acid, and the like. The steps to effect resolution by this procedure involve mixing a solution of the salt with seed crystals of the salt of the desired enantiomer of ACL. At the same time free ACL and a catalyst which racemizes ACL are introduced.

Since exchange between free ACL and ACL salt is rapid in solution, racemization of ACL results in racemization of the ACL salt also. Certain precautions of a practical nature are preferably adhered to in the course of this resolution/racemization process:

The catalyst should remain in solution while the L-ACL salt crystallizes which normally requires that dilute concentrations of catalyst be employed.

Because at low catalyst levels the racemization is slow at the temperatures (30°–45°C.) at which resolution has been demonstrated, it is necessary that the reaction be conducted at temperatures higher than 45°C. in order to have a sufficiently high racemization rate. However, at increased temperatures, precautions against the adverse effect of elevated temperature on resolution must be considered. Accordingly, the lowest temperature consistent with suitable racemization and as determined by the catalyst utilized should be employed.

Illustrative catalysts which may be employed in the salt/ACL mixtures are the following:

A. Complexes of salen* derivatives with $Fe^{++}$ or $Co^{++}$ e.g. $Fe^{II}$ (5-nitrosalen)

*N,N'-ethylenebis(salicylideneimine)

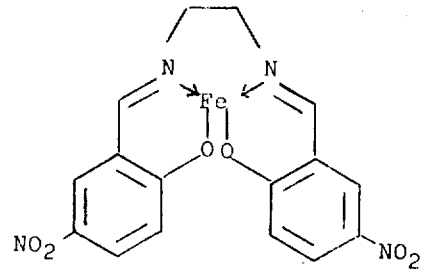

B. Derivatives of chelating carbonyl compounds and metal ions $M^{n+}$, e.g. $Fe^{2+}$, $Fe^{3+}$, $Al^{3+}$, $Cu^{2+}$, $Ni^{2+}$ and the like.

The following is illustrative of a suitable mechanism for racemization of ACL catalyzed by chelating carbonyl compounds of this kind:

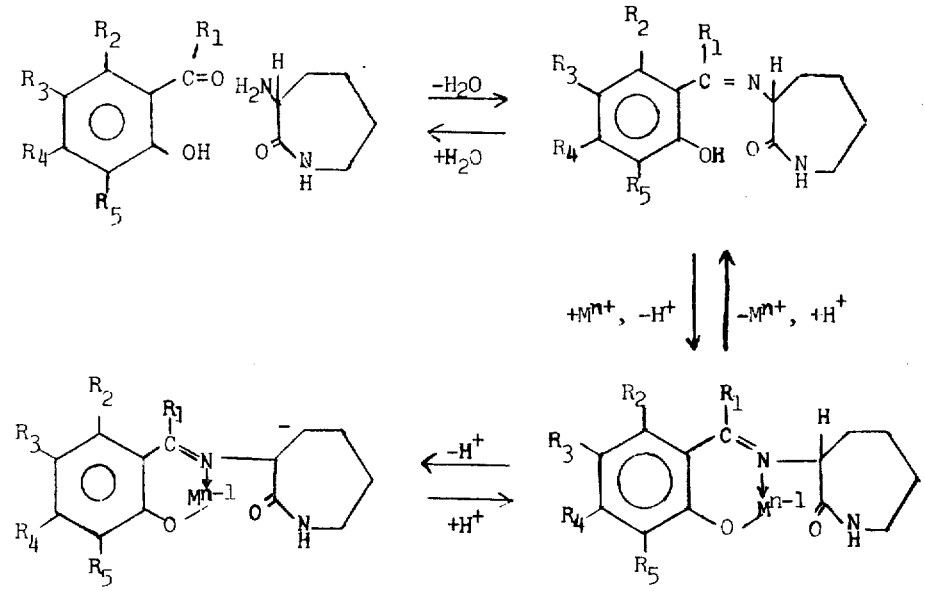

wherein $R_1$ is H, alkyl or cycloalkyl and $R_2$ through $R_5$ are H, $-NO_2$, a halogen, $-CN$, $-COOH$, $-OCH_3$ substituents.

Reaction of the carbonyl group of the catalyst with the amino group of D or L -ACL results in reversible formation of a Schiff base. The Schiff base can complex reversibly with a metal ion, $M^{n+}$, wherein $n$ has a value of 2 or 3. The resulting complex has a highly labile proton in the α-position of the α-ACL moiety. This proton can be abstracted by a weak base, e.g. α-ACL, resulting in the production of a carbanion of the Schiff base complex which has no asymmetry. Return of the proton to the carbanion can form either L- or D- Schiff base complex, therefore the net result is racemization. Since all the steps of this mechanism are reversible, only catalytic amounts of the chelating carbonyl compound and the metal ion are sufficient to cause racemization of all the α-ACL present.

Certain of said Schiff bases as well as metal complexes, noted hereinbelow in greater detail, are novel compositions of matter. Illustrative of such novel compositions are the metal complexes of Schiff bases of aminolactam with chelating carbonyl compounds such as salicylaldehyde, 5-nitrosalicylaldehyde and orthohydroxyacetophenone. The following procedure describes the synthesis of compositions of this kind, i.e. bis[N-(D,L-hexa-hydro-2-oxo-2H-azepin-3-yl)-5-nitrosalicylaldiminato]iron (III) chloride, $Fe^{III}(5\text{-}NO_2.Sal^*.ACL)_2Cl$.

* salicylaldehyde

In essentially the same manner the following additional complexes were prepared:

$Fe^{III}(Sal.ACL)_2Cl$, $Fe^{III}(5\text{—}NO_2.Sal.ACL)_3$, $Cu^{II}(5\text{—}NO_2Sal.ACL)_2$, $Zn^{II}(5\text{—}NO_2Sal.ACL)_2$ Preparation of $Fe(5\text{—}NO_2Sal.ACL)_2Cl$ Ferric chloride hexahydrate (405 mg., 1.5 mmol) was dissolved in 15 ml methanol, then 5-nitrosalicylaldehyde (501 mg., 3 mmol) was added and the mixture heated to boiling to dissolve the aldehyde. To the boiling solution was added a hot solution of D,L-α-aminocaprolactam (768 mg., 6 mmol) in 5 ml ethanol. The dark red solution was allowed to cool to room temperature and stand for several hours, then the dark maroon crystals were collected by filtration. The crystals were washed with ethanol, water, ethanol, and finally with ether, then dried in vacuo at 70°C. Yield: 533 mg. (55%). Decomposes but does not melt at 280°. Analysis: Calcd. for $C_{26}H_{28}ClFeN_6O_8.H_2O$: C, 47.18; H, 4.57; N, 12.70; Cl, 5.36; Fe, 8.44. Found: C, 47.29; H, 4.55; N, 12.42; Cl, 4.99; Fe, 8.2.

The complexes can be prepared directly from the Schiff bases themselves which are also novel compositions of matter. The Schiff bases which are suitable are those derived from the reaction of aminocaprolactam with salicylaldehyde or substituted salicylaldehydes in which the substituent is an electron withdrawing group. Illustrative substituted salicylaldehydes are 5-nitrosalicylaldehyde, 4-nitrosalicylaldehyde, 3-nitrosalicylaldehyde, 5-chlorosalicylaldehyde, 4-chlorosalicylaldehyde, 3-chlorosalicylaldehyde, 5-bromosalicylaldehyde, 4-bromosalicylaldehyde, 3-bromosalicylaldehyde, 5-cyanosalicylaldehyde, 4-cyanosalicylaldehyde, 3-cyanosalicylaldehyde, 3,5-dinitrosalicylaldehyde, 3,5-dichlorosalicylaldehyde, 3,5-dibromosalicylaldehyde, 3,5-dicyanosalicylaldehyde, 3,5-diacetylsalicylaldehyde, and the like. A typical preparation is described below for the Schiff base of 5-nitrosalicylaldehyde and aminocaprolactam:

Preparation of N-(5-nitrosalicylidene)-D,L-α-amino-ε-caprolactam or alternatively N-(5-nitrosalicylidene)-D,L-3-aminohexahydro-2H-azepin-2-one.

5-Nitrosalicylaldehyde (6.7g, 40 mmol) was dissolved in 75 ml boiling ethanol and treated with a hot solution of D,L-α-aminocaprolactam (5.1g, 40 mmol) in 25 ml ethanol. The reaction mixture was allowed to cool to room and stand for 0.5 hour, during which time the organic product was crystallized from solution. The crystals were collected by filtration, washed with ethanol and dried in vacuo at 60°. Yield: 9.5g (86%) mp 204–207 (dec.) Analysis: Calcd. for $C_{13}H_{15}N_3O_4$: C, 56.31; H, 5.45; N, 15.15. Found: C, 56.21; H, 5.71; N, 14.92.

In a similar manner, the Schiff base of salicyladehyde and aminocaprolactam was prepared to yield N-salicylidene-D,L-α-amino-ε-caprolactam or alternatively N-salicylidene-D,L-3-aminohexahydro-2H-azepin-2-one.

Another method of effecting a single stage resolution/racemization involves the preferential crystallization of a diastereomer salt of the desired enantiomer of ACL. Use of seed crystals of the same diastereomeric structure is optional in this embodiment because the desired diastereomeric salt is inherently substantially less soluble than the undesired diastereomeric salt.

Several such diastereomeric salts are known which may be utilized including the following:

L-ACL.L-pyrrolidonecarboxylic acid
L-ACL.D-N-carbamoylvaline
L-ACL.L-N-p-nitrobenzoylglutamic acid
L-ACL.L-N-benzoylglutamic acid
L-ACL.L-N-p-toluylglutamic acid
L-ACL.L-N-p-chlorobenzoylglutamic acid and the like.

The steps employed in effecting resolution via this embodiment comprise:

a. forming diastereomeric salts of ACL by reaction with one enantiomer form of an asymmetric acid in a suitable solvent;

b. preferentially crystallizing the diastereomeric salt of the desired enantiomer of ACL and separating this preferred salt. Simultaneously, the undesired enantiomer of the ACL is racemized in solution.

The catalyst systems utilized may be those described hereinabove with reference to a system which employs an enantiomeric salt. Also, the considerations outlined in connection with the above enantiomer salt and concerning utilization of dilute catalyst concentration apply also in general in this alternative. Moreover in connection with the use of diastereomeric salts the optically active acid used to form the L-ACL diastereomeric salt must not racemize substantially under the conditions of ACL racemization/resolution.

The invention will be further described by the following examples:

EXAMPLE 1

A sample of 0.702g. (2.74 mmol) of L-ACL, 1.100g (4.30 mmol) of D,L-ACL, 3.10 ml (2.00 mmol) of $NiCl_2$ and 1.0 ml (0.3 mmol) of sodium methoxide in ethanol were adjusted with ethanol to 10.0 ml. The molar ratio of ACL to $NiCl_2$ in this solution is 3.5. To obtain other $ACL/NiCl_2$ ratios as shown in Table I, the amounts of sample L-ACL and D,L-ACL were increased accordingly. Samples of 2.0 ml each of the solution were sealed and placed in a 60°C. (50° and 40°) bath. At different time intervals the samples were taken from the bath to determine the extent of racemization of L-ACL. To this end each sample was quenched and adjusted to 5.0 ml with 1N.HCl. The results of these experiments which are presented in Table I show that the racemization rate increases with increasing temperature and up to a point, with increasing ACL/NiCl$_2$ ratio. The latter correlation is indicative of the importance of rendering Ni$^{++}$ coordinately saturated. It should be noted that even at temperatures as low as 40°C. suitable reaction rates are obtained and, in general, a temperature range of about 40° to about 95°C. may be used.

TABLE I[a]

| ACL/NiCl$_2$ mole ratio | Solvent | Temperature °C. | Racemization Rate $t_{1/2, min.}$ |
|---|---|---|---|
| 3.5 | Ethanol | 60 | 70 |
| 4 | Ethanol | 60 | 43 |
| 5 | Ethanol | 60 | 26 |
| 6 | Ethanol | 60 | 22 |
| 3.5 | Methanol | 50 | 340 |
| 4 | Methanol | 50 | 260 |
| 5 | Methanol | 50 | 162 |
| 6 | Methanol | 50 | 170 |
| 3.5 | Methanol | 40 | 1004 |
| 4 | Methanol | 40 | 770 |
| 5 | Methanol | 40 | 583 |
| 6 | Methanol | 40 | 614 |

[a]Concentration of NiCl$_2$ is 0.20 M.

EXAMPLE 2

A solution was made containing 3.84g (30 mmol) of L-ACL, 1.48g (10 mmol) NiCl$_2$.H$_2$O and 0.081g (1.5 mmol) of NaOCH$_3$ in 50 ml methanol. Aliquots of this solution, 2 ml each, were placed in screw-cap vials. A measured quantity of a complexing agent was also added to each vial, which was then placed in a bath thermostated at 70°C. The extent of racemization was measured at various time intervals and the half-life of reaction was calculated. The results which appear in the following table show that complexing agents other than ACL can be used to render the (ACL)$_3$NiCl$_2$ complex coordinately saturated resulting in rapid racemization in the presence of a strong base.

TABLE II

Racemization of (L-ACL)$_3$NiCl$_2$ in MeOH at 70°C.[a]

| Sample No. | Complexing Agent | Mole of Complexing Agent per mole of (L-ACL)$_3$NiCl$_2$ | $t_{1/2}$, min. |
|---|---|---|---|
| 1 | none | — | 433 |
| 2 | ACL | 1.0 | 20 |
| 3 | NH$_3$ | 2.1 | 58 |
| 4 | ethylene-diamine | 1.0 | 9 |
| 5 | sodium lysinate | 1.0 | 11 |
| 6 | 1,10-phenanthroline | 1.0 | 19 |

[a]in the presence of 15 mol % NaOCH$_3$

EXAMPLE 3

Racemization of (L-ACL)$_3$NiCl$_2$ Solution in the Presence of (L-ACL)$_3$ NiCl$_2$ Crystals A 1.11g (2 mmol) sample of (L-ACL)$_3$NiCl$_2$ was added to a solution of 264 mg (2.1 mmol) D,L-ACL and 0.3 ml 1M ethanolic KOH (0.3 mmol) in a total of 4.4g ethanol. The mixture was heated to reflux and stirred continuously. A portion of the crystals dissolved. After 1 hour the mixture still remained substantially heterogeneous; the slurry (solid and liquid) was sampled, evaporated to dryness, and the optical rotation obtained. The result showed 70% racemization of L-ACL. Refluxing was continued for 4.5 hours, but the mixture remained heterogeneous. A sample of the slurry proved to be only 73% racemized, that is, no significant change from the earlier sample. The remaining slurry was filtered and the optical purity of the crystals was determined and found to be 100%. The mother liquor was essentially racemic. This experiment demonstrates that optically active crystals of (L-ACL)$_3$NiCl$_2$ do not racemize under conditions that cause dissolved (L-ACL)$_3$NiCl$_2$ to racemize.

EXAMPLE 4 a. A 20 ml ethanol solution containing 8 mmol (D,L-ACL)$_3$NiCl$_2$ and 8 mmol D,L-ACL was passed through a strongly basic [quaternary ammonium hydroxide type (ANGA-542*)] ion exchange column in about 1 hour. The complex solution was followed by 15 ml ethanol and the combined eluent brought to 50 ml in a volumetric flask. Titration of an aliquot indicated a total of 9.8 meq Cl$^+$, which indicates that 6.2 meq of $^-$OH (or $^-$OEt) had been incorporated into the complex solution).

* supplied by J. T. Baker Company

A reaction solution was prepared from 0.518g (2 mmol) of 50% L-ACL (88% optically pure) in ethanol, 1.13g (4.4 mmol) 50% D,L-ACL in ethanol and 2.48 ml 0.645 M in NiCl$_2$.H$_2$O in ethanol. This was brought to reflux and 2.5 ml of the solution described above was added. The final quantities thus are total ACL 8 mmol, Ni$^{+2}$, 2 mmol, $^-$OH (free or bound to Ni$^{+2}$), 0.3 mmol and Cl$^-$. 3.7 Mmol, in a total volume of 6.7 ml. The kinetics of racemization were determined at reflux (~80°C.) and gave k=1.1×10$^{-3}$ sec.$^{-1}$ or $t_{1/2}$=10.5 min.

Analysis of the reaction mixture by thin layer chromatography (TLC) showed the presence of small amounts of lysine byproduct (about 1 mol % of ACL after 1 hour of reflux).

b. A 10 ml sample of 0.90 M NiCl$_2$. H$_2$O in ethanol, was passed through a weakly basic ion exchange resin (IR-45, supplied by Rohm and Haas Company). The eluent had pH 5.5 (measured with a glass electrode in ethanol; the pH of untreated NiCl$_2$ solution was about 3.7). A 1 ml aliquot of the eluent, containing 0.15 m atoms of Ni$^{++}$, was mixed with 78 mg (0.60 mmols) of L-ACL in 1 ml methanol. The mixture was heated in a sealed vial at 80°C. for 30 minutes. Subsequent determination of optical activity in 1N HCl showed that the mixture had completely racemized.

EXAMPLE 5

Batch Simultaneous Resolution/Racemization of (D,L-ACL)$_3$NiCl$_2$

A 0.556g sample of NiCl$_2$, anhydrous (4.3mmol) in 6.1g ethanol was heated at reflux, then 2.05g (16 mmol) solid D,L-ACL was added and the mixture heated at reflux for 2 hours to dissolve the nickel chloride. The solution was filtered to remove 10 mg. of undissolved solids. A 0.60 ml sample of 0.99 M.KOH in ethanol was added, the solution stirred 10 minutes, then filtered to remove KCl. The solution was again heated and 3.2 ml. ethanol distilled out, leaving a solution containing about 33% complex by weight. A 200 mg sample of (L-ACL)$_3$NiCl$_2$ (100% optically pure) was added and the flask heated at 85°–90° for 1.5 hours, with occasional stirring. The crystals were collected by filtration, washed with ethanol and dried in vacuo at 60°. Yiled: 646 mg, $[\alpha]_D$–22.3°, ($c$=4, 1N HCl) 95% optically pure. This represents 20% resolution with respect to the available complex. The mother liquors from the filtration were diluted to 25 ml with 3 ml 6N HCl and the remainder 1N HCl. The observed optical rotation $\alpha_{obs}$=+0.01° corresponds to a 10 mg excess of (D-ACL)$_3$NiCl$_2$ in solution and indicates essentially complete racemization. Analysis of the mother liquor by TLC showed the absence of lysine.

EXAMPLE 6

Batch Simultaneous Resolution/Racemization of (D,L-ACL)$_3$NiCl$_2$

A 0.556g sample of NiCl$_2$.½H$_2$O (4 mmol) In 6.1g ethanol was heated to reflux, then 2.07g (16 mmol) solid D,L-ACL was added and the mixture heated at reflux for 1 hour to dissolve the nickel chloride. A 0.60 ml sample of 0.99 M KOH in ethanol was added, the solution stirred 10 min., then filtered to remove KCL. The solution was again heated and 3.2 ml ethanol distilled out, leaving a solution containing about 33% complex by weight. A 200 mg sample of (L-ACL)$_3$NiCl$_2$ (100% optically pure) was added and the flask heated at 85°–90° for 1.5 hours, with occasional stirring. The crystals were collected by filtration, washed with ethanol and dried in vacuo at 60°. Yield: 648 mg, $[\alpha]_D$=–22.2°, ($c$=4, 1N HCl) 95% optical purity. This represents 20% resolution with respect to the available complex. The mother liquors from the filtration were diluted to 25 ml with 3 ml 6N HCl and the remainder 1N HCl. The observed optical rotation, $\alpha_{obs}$=+0.01°, corresponds to a ~10mg excess of (D-ACL)$_2$NiCl$_2$ in solution and indicates essentially complete racemization. Analysis of the mother liquor by TLC shows the presence of small amounts of lysine by-product (i.e. about 1.5 mol % of ACL).

EXAMPLE 7

Simultaneous Resolution/Racemization with Addition of Makeup Solution and Solvent Removal a. An initial feed solution was prepared from 15.2 ml (10.5 mmol) 0.69 M NiCl$_2$.H$_2$O in ethanol, 1.072g (42 mmol) 50% D,L-ACL in ethanol, 0.72 ml (1.58 mmol) 2.19 M NaOEt and 2.7 ml ethanol, a total volume of 30 ml.

A makeup solution was prepared from 16.8 ml (11.6 mmol) 0.69 M NiCl$_2$.H$_2$O solution, 9.23g (36 mmol) 50% D,L-ACL solution, 0.16 ml (0.35 mml) 2.19 M NaOEt and 3.2 ml ethanol, a total volume of 30 ml.

The starting solution was placed in a 50 ml 3-neck round-bottom flask fitted with mechanical stirrer, addition funnel and distillation head. The flask was immersed in an oil bath at 120° and 1.50g (L-ACL)$_3$NiCl$_2$ seeds added. The average size of the seed crystals was 3.6$\mu$. The makeup solution was slowly added to the flask at the same rate as ethanol was distilled out; this required 1.5 hours. Then the reaction mixture was filtered and the crystals washed with ethanol and dried in vacuo at 75°. Yield: 0.717g(50% of available complex) $[\alpha]_D$–22.1° ($c$=4, 1N HCl) or 94% optical purity. The average size of the product crystals was 5.3$\mu$.

The mother liquor weighed 19.32g, of which 6.2g was (ACL)$_3$NiCl$_2$ complex. A 1.0g sample in 5 ml 1N HCl had $[\alpha]_D$=+2.3°; this corresponds to 7.4% optial purity in D-isomer based on the total ACL in solution. Small amounts of lysine were also present in the mother liquor.

b. The experiment was repeated varying the time, the lactam to nickel ratio and the size of the crystal seeds, i.e. using an ACL/Ni molar ratio of 5/1 and was completed in 52 minutes. The seeds used in this experiment had an average size of 6.8$\mu$. The crop was 92% optically pure and represented 35% of the available complex. The mother liquor had a 7.2% excess of D-ACL. In this experiment, small amounts of lysine were also present in the mother liquor.

EXAMPLE 8

Resolution/Racemization of (D-ACL)$_3$NiCl$_2$

A solution containing 0.590g NiCl$_2$.H$_2$O (4 mmol), 2.05g (16 mmol) D,L-ACL and 0.033g (0.6 mmol) KOH in 4.9g ethanol is heated at reflux, then 202 mg (D-ACL)$_3$NiCl$_2$ seed crystals are added. The mixture is held for 75 minutes at reflux with gentle stirring, then filtered, the crystals washed with cold ethanol and dried in vacuo at 60°. A crop weighing 261 mg and having 97% optically pure (D-ACL)$_3$NiCl$_2$ is obtained. The mother liquor shows negligible optical activity, indicating essentially complete racemization.

EXAMPLE 9

Semicontinuous Resolution/Racemization of (ACL)$_3$NiCl$_2$

For this experiment a reactor vessel consisting of a 190 ml 3-neck round-bottom flask equipped with a stopcock on the bottom for sampling the reaction mixture was employed. Samples were taken directly into interchangeable sintered-glass filter funnels where they were filtered under nitrogen pressure. Means were provided for washing the crystals on the filter. A tubing from the bottom of the filter automatically returned the mother liquid to the reaction vessel; a small port was provided for sampling the liquor in this tubing. The flask was equipped with a mechanical stirrer and a distillation head; a tube from a reservoir of make-up solution passed through the distillation head into the flask. The third neck of the flask was used for addition of the seed crystals. The flask was wrapped with heating tape for maintaining the desired temperature.

The initial charge was a 108 ml ethanol solution prepared from 55.7 ml (36 mmol) 0.646 M NicL$_2$.H$_2$O in ethanol, 23.1g (180 mmol) D,L-ACL and 2.76 ml (5.4 mmol) 1.96 M NaOEt. Makeup solutions were prepared from 55.7 ml (36 mmol) 0.646 M NiCl$_2$.H$_2$O ethanol solution, 14.3 g (111.6 mmol) D,L-ACL 1.10 ml (2.16 mmol) 1.96 M NaOEt and sufficient ethanol to make a total of 100 ml. Two such makeup solutions were prepared.

The initial charge was introduced into the reactor and the solution brought to reflux, then 8.7g (L-ACL)$_3$NiCl$_2$ seed crystals of 97% optical purity were added. The average size of the seed crystals were 6.8 $\mu$. After 10 minutes, addition of the first makeup was started and after addition was half complete the first sample (ca 25 ml) was filtered and 1.5g seed crystals added. Sampling was repeated after each 25 ml addition from that point and was always accompanied by addition of 1.5g seeds, of same size as above. The time of addition was adjusted to approximately 80 minutes per 100 ml. Throughout the operation ethanol was distilled off at a rate which was adjusted to maintain the volume of the reacion mixture approxmately constant at 100 ml. Each sample was analyzed as follows: The crystalline cake obtained from filtration of the sample was dried in vacuo, weighed and optical rotation was determined in 1N HCl. The mother liquor was analyzed for Cl⁻ and for optical rotation. From this analysis it was possible to determine the enantiomeric excess of D-ACL Ni complex in solution. The data are presented in Table III. After 203 min. a total of 200 ml of makeup solution had been introduced to the reactor, besides the initial charge of 108 ml. and 7 samples had been withdrawn. At that point the volume of the reaction mixture was reduced to about 80 ml. by evaporation of ethanol and the residue, after refluxing for about 30 more minutes, was filtered.

hot. The crystals were washed with ethanol and dried in vacuo at 60°C. Yield: 0.94g (31% recovery) $[\alpha]_D = -24.2$ ($c=4$, 1N HCl), 100% optical purity. The run illustrates that 100% optically pure crystals of (L-ACL)$_3$NiCl$_2$ of seed quality can be obtained from optically impure product.

b. In a similar manner, (L-ACL)$_3$CoCl$_2$ of 96% optical purity was obtained by partially dissolving 91% optically pure (L-ACL)$_3$CoCl$_2$ in refluxing ethanol. Recovery in this case was 78%, i.e. 22% was dissolved. In some cases up to 90% or more of the optically impure complex may be dissolved in an alcohol or water or mixtures thereof, in effecting the optical purification.

EXAMPLE 11

Decomposition of (L-ACL)$_3$NiCl$_2$ with HCl (L-ACL)$_3$NiCl$_2$, 95% optically pure, 4.37g (7.8 mmole) was dissolved in 10.0 g (12.6ml) methanol at reflux. Then 2 ml ethanol was added and the solution was acidified by bubbling in anhydrous HCl. The mix-

TABLE III

| Time | Feed, ml | Semicontinuous Resolution/Racemization of (D, L-ACL)$_3$NiCl$_2$(a) | | | | | |
|------|----------|-------------|---------|-------------|------|------|------------------|
| | | Mother Liquor | | | Crop | | |
| | | Cl⁻, meq. | [d]°D | %D in excess | Wt,g | [d]$_D$ | Optical Selectivity$^d$ |
| 0 | 108, init charge | | | | | | |
| 10 min | 8.7g seed | | | | | | |
| 46 | 50$^b$ | 1.422/10ml | +1.32° | 3.9 | 3.04 | −22.4 | 96.5 |
| 67 | 75$^b$ | 1.312 | +1.19° | 3.5 | 4.99 | −21.6 | 93.5 |
| 87 | 100$^b$ | 1.312 | 0 | 0 | 3.62 | −21.6 | 93.5 |
| 110 | 125$^b$ | | | | 4.11 | −22.3 | 96.5 |
| 130 | 150$^b$ | 1.664 | +1.78° | 5.2 | 5.25 | −21.7 | 93.9 |
| 155 | 175$^b$ | | | | 5.08 | −22.0 | 95.2 |
| 172 | 200$^b$ | 1.278 | +1.34° | 3.9 | 4.38 | −21.7 | 93.9 |
| 203 | e | | | | | | |
| 238 | f | 2.31 | +0.68° | 2.0 | 28.09 | −21.9 | 94.8 |

$^a$ Volume of reaction mixture approximately 100 ml.
$^b$ Sample taken, 1.5 g seed added. Volume shown is cumulative exclusive of initial charge.
$^c$ Based on 5ACL:2Cl⁻
$^d$ Based on $\alpha_d = -23.1°$ for the seeds.
$^e$ Volume of reaction mixture reduced to 80 ml by evaporation.
$^f$ Reaction stopped; reaction mixture filtered.

TLC analysis of this final mother liquor indicated about 1.5% lysine based on the total ACL charged in the course of the experiment. The combined crops had a specific rotation of $[\alpha]_D = -21.6$ ($c=4$, in 1N HCl) or 91% optical purity. Since the seeds used were 97% optically pure, the optical selectivity was 94%. The combined crops weighed 58.56g.

A similar experiment carried out using 4:1 ratio in the reaction mixture and using 100% optically pure seed crystals of 3.6μ size, ACL:NiCl$_2$ ratio of 4:1 and a 1 hr. addition time was not as successful as above described run, due largely to a buildup of excess D-complex in the reactor, amounting to as much as a 30% excess. The average optical purity of the crystals produced was 90% with an average seed size of 5.3μ. This indicates that when the crystallization of (L-ACL)$_3$NiCl$_2$ is carried out at a rate which is substantially higher than the rate of racemization, the optical selectivity of the overall process is adversely affected.

EXAMPLE 10

Optical Purificaion of (L-ACL)$_3$NiCl$_2$ and (L-ACL)$_3$CoCl$_2$ a. A 3.0g sample of (L-ACL)$_3$NiCl$_2$, 91% optically pure obtained as the product of Example 9, was refluxed for 15 minutes with 4.5g methanol, then filtered ture heated spontaneously to about 40°C. The color changed from deep blue to light green and white crystals of L-ACL.HCl appeared. The mixture was cooled to 25°C., maintained at that temperature for 5 minutes and filtered; the crystals were washed with a little ethanol and dried at 120°C. A yield of L-ACL.HCl 3.50g (21.3 mmol) 100% optically pure was obtained. This corresponds to 91% of charge (96% of available L-excess). The experiment demonstrates that optically pure L-ACL.HCl can be obtained by the decomposition of optically impure (L-ACL)$_3$NiCl$_2$.

EXAMPLE 12

Batch Simultaneous Resolution/Racemization of (ACL)$_3$CoCl$_2$

A solution was prepared by refluxing 0.77g (6 mmol) DL-ACL, 0.19g (1.5 mmol) CoCl$_2$ and 0.016g (0.23 mmol) NaOC$_2$H$_5$ with 25ml of anhydrous ethanol. The solution was cooled to 40°C., then a 0.030g sample of (L-ACL)$_3$CoCl$_2$, $[\alpha]_D = -23.9°$ ($c=4$, 1N HCl) was added and the mixture was allowed to stand for 15 hours at 35° to 40°C. Then the reaction mixture was filtered and the crystals were washed with ethanol and dried in vacuo at 60°C. Yield of (L-ACL)$_3$CoCl$_2$ was 0.212g $[\alpha]_D = -22.9°$ ($c=4$, 1N HCl), therefore the optical selectivity was 96% and the resolution 22% with respect to the total $(ACL)_3CoCl_2$ in solution. The mother liquor had $[\alpha]_D=0°$, indicating complete racemization of the D-ACL in solution.

EXAMPLE 13

A solution containing 0.160g (1.25 mmol) L-ACL, 0.206g (1.25 mmol) L-ACL.HCl and 0.15 mols of $Cu^{II}$ (5-nitrosalicylaldehyde)$_2$ in 20/80 (v/v) H$_2$O/dimethylformamide (10 ml overall volume) was heated for 15 minutes at 70°C. An aliquot of the reaction mixture was diluted with 1N hydrochloric acid and had no optical rotation, indicating complete racemization (detectability limit for L-ACL excess in solution was 0.003g).

EXAMPLES 14–42

Following the procedure of Example 13, racemization of L-ACL.HCl was conducted in the presence of various catalysts and under various conditions of temperature and concentration; the data is summarized in Table IV.

TABLE IV

Racemization of L-ACL.HCl/L-ACL

| Example | Catalyst mole/100 mole (ACL.HCl + ACL) | | ACL.HCl/ACL $^{(a)}$mole ratio | Solvent volume ratio | Temp °C | $t_{1/2}$ min |
|---|---|---|---|---|---|---|
| 14 | FeCl$_2$, | 6.0 sal 12.0 | 2.0 | H$_2$O/DMF 20/80 | 70 | 44 |
| 15 | " | " | 1.0 | " | " | 13 |
| 16 | " | " | 0.50 | " | " | 10 |
| 17 | " | " | 0.33 | " | " | 28 |
| 18 | CuCl$_2$ 6.0, | " | 2.0 | " | " | 44 |
| 19 | " | | 1.0 | " | " | 16 |
| 20 | " | " | 0.50 | " | " | 7 |
| 21 | " | " | 0.33 | " | " | 9 |
| 22 | AlCl$_3$ 6.0, | " | 2.0 | " | " | 200 |
| 23 | " | " | 1.0 | " | " | 34 |
| 24 | " | " | 0.50 | " | " | 18 |
| 25 | " | " | 0.33 | " | " | 16 |
| 26 | CuCl$_2$ 6.0, 5-NO$_2$-sal 12.0 | | 0.33 | " | " | 2 |
| 27 | AlCl$_3$ 0.6, 5-NO$_2$-sal 1.7 | | 1.0 | H$_2$O/DMF 25/75 | " | 7 |
| 28 | ZnCl$_2$ 0.6, 5-NO$_2$-sal 1.2 | | 1.0 | " | " | 107 |
| 29 | FeCl$_2$ 0.6, 5-NO$_2$-sal 1.2 | | 1.0 | " | " | 2 |
| 30 | FeCl$_2$ 0.6, 5-NO$_2$-sal 1.7 | | 1.0 | " | " | 1 |
| 31 | " | | 1.0 | H$_2$O/MeOH 10/90 | 65 | 7 |
| 32 | FeCl$_3$ 0.6, 5-NO$_2$-sal 1.1 | | 1.0 | H$_2$O/MeOH 10/90 | 65 | 8 |
| 33 | FeCl$_3$ 0.6, 5-NO$_2$-sal 1.9 | | 0.26 | " | " | 4 |
| 34 | FeCl$_3$ 0.6, 5-NO$_2$-sal 3.0 | | 0.26 | " | " | 5 |
| 35 | FeCl$_3$ 0.3, 5-NO$_2$-sal 0.3 | | 0.26$^{(b)}$ | " | " | 54 |
| 36 | FeCl$_3$ 0.3, 5-NO$_2$-sal 1.5 | | 0.26$^{(c)}$ | " | " | 13 |
| 37 | Fe$^{II}$ (salen) 6.0 | | 2.0 | H$_2$O/DMF 20/80 | 70 | 15 |
| 38 | " | | 1.0 | " | " | 8 |
| 39 | " | | 0.50 | " | " | 8 |
| 40 | " | | 0.33 | " | " | 7 |
| 41 | Fe$^{II}$(5-NO$_2$ salen) 6.0 | | 1.0 | " | " | 4 |
| 42 | " | | 0.33 | " | " | 2 |

$^{(a)}$Concentration of ACL.HCl + ACL equal to 0.25 M, unless otherwise noted
$^{(b)}$ACL.HCl + ACL = 0.33 M
$^{(c)}$ACL.HCl + ACL = 1.75 M
Abbreviations:
sal = salicylaldehyde; 5-NO$_2$sal = 5-nitrosalicylaldehyde
salen = ethylene-N,N'-bis(salicylideneimine)5-NO$_2$ salen = ethylene-N-N'-bis(5-nitrosalicylideneimine)

EXAMPLES 43–45

The procedure of Example 13 was essentially repeated using L-ACL.β-naphthalene sulfonate (L-ACL.NSA) instead of L-ACL.HCl. The data and results are summarized in Table V.

TABLE V

Racemization of L-ACL.NSA/L-ACL

| Example | Catalyst mole/100 mole (ACL.NSA + ACL) | | ACL.NSA/ACL $^{(a)}$mole ratio | Temp °C | $t_{1/2}$ min |
|---|---|---|---|---|---|
| 43 | FeCl$_3$ | 0.5 | N-NO$_2$sal$^{(b)}$ 3.0 | 1.0 | 65 | 31 |
| 44 | " | 1.0 | " | " | " | 35 |
| 45 | " | 0.5 | " | " | 70 | 25 |

$^{(a)}$Concentration of L-ACL.NSA + L-ACL equal to 0.30 M in methanol
$^{(b)}$5-NO$_2$sal = 5-nitrosalicylaldehyde

EXAMPLE 46

D,L-ACL.HCl, 236mg, D,L-ACL, 693mg and 0.5ml of a racemization catalyst solution containing 5.95mg/ml $FeCl_3.6H_2O$ and 22.2mg/ml 5-nitrosalicylaldehyde in methanol, were mixed with 0.9ml methanol and heated at 80°C. in a sealed vial. The resulting homogeneous solution was cooled to 65°C., then 50mg. of L-ACL.HCl seed crystals were added and the temperature was dropped to 60°C. within 10 minutes and maintained at that temperature for an additional 10 minutes. The grown crystals were filtered, washed with ethanol and dried in vacuo at 60°C. Yield of L-ACL.HCl was 120mg of optical purity 65%. This represents a gain of 16mg of L-ACL.HCl. The mother liquor had no optical rotation, indicating that racemization took place; the D-ACL excess in solution was less than 9mg limit of detectability.

EXAMPLE 47

Simultaneous Resolution/Racemization of ACL.β-naphthalenesulfonate

D,L-ACL, 1.51 g, and D,L-ACL.β-naphthalenesulfonate, 3.90g, were dissolved in 25ml methanol at reflux. Then 10 ml methanol were distilled off and 1 ml methanol solution containing 15.8 mg $FeCl_3.6H_2O$ and 58.6 mg 5-nitrosalicylaldehyde was added. Then 0.50g of L-ACL.β-naphthalenesulfonate seed crystals were added and methanol was distilled off at the rate of about 0.1 ml/min. After 1 hour, 6 ml methanol had been distilled off. Heating was continued for an additional period of 10 minutes. The grown crystals were filtered, washed with a little methanol and dried in vacuo at 60°C. Yield of L-ACL.β-naphthalenesulfonate was 0.97 g of optical purity 93%. This corresponds to 0.40 g. gain in L-salt. Examination of the mother liquor showed the presence of less than 0.10 g D-salt excess in solution, indicating the occurrence of racemization simultaneously with the resolution.

EXAMPLE 48

Simultaneous Resolution/Racemization of ACL via Diastereomeric Salt With L-Pyrrolidonecarboxylic acid (L-PCA)

D,L-ACL, 2.56 g (20 mmol) was dissolved in 31 ml of refluxing glyme, then a racemization catalyst solution of 16.6 mg (0.1 mmole) $FeCl_3$ and 5.31 mg (0.3 mmole) 5-nitrosalicylaldehyde in 5 ml glyme was added. Next a solution of 1.28 g (9.9 mmole) L-PCA in 75 ml of hot glyme was added with stirring while maintaining reflux. A crystalline precipitate formed. Next the mixture was refluxed and stirred for 1 hour, filtered hot, the crystals were washed with glyme and dried in vacuo at 60°C. Yield of L-ACL.L-PCA salt was 2.61 g (theoretical is 2.56 g). A 1.30 g aliquot of the salt was slurried with 15 ml isopropanol and decomposed with 1 m of 12 N-hydrochloric acid, L-ACL.HCl, 0.824 g (99% of theory) was obtained, $[\alpha]_D = -20.1°$ ($c=4$, 1N HCl). This corresponds to 76% optical purity of L-ACL.

The mother liquor from the diastereomer salt filtration was treated with 1 ml of 12 N-HCl in glyme. ACL.HCl, 1.48 g (87% of theory) was obtained, $[\alpha]_D = +0.7$ ($c=4$, 1N HCl). This indicates that the ACL in the mother liquor was about 96% racemic.

EXAMPLE 49

Example 48 was repeated except that the L-PCA was added dropwise during a period of 2 hours. A total of 18 mmole L-PCA was used or 90 mole % with respect to total ACL charged. The L-ACL.HCl obtained by decomposition of the crystalline L-ACL.L-PCA was 15 mmole (or 75% of the total ACL charged) of 82% optical purity.

It is to be understood that variations and modifications of the present invention will be apparent to those skilled in the art from the foregoing and such variations and changes may be made without departing from the scope of the invention. It is also to be understood that the scope of the invention is not to be interpreted as limited to the specific embodiment disclosed herein, but only in accordance with the appended claims when read in light of the foregoing disclosure.

We claim:

1. A process for effecting transformation of a D,L-aminocaprolactam compound selected from the group consisting of
    A. the D,L-aminocaprolactam complexes, (tris-aminocaprolactam)nickel (II) salts and (tris-aminocaprolactam)cobalt(II) salts,
    B. the D,L-aminocaprolactam salts of the acids hydrogen chloride, hydrogen bromide, β-naphthalenesulfonic acid and 2-naphthylamine-1-sulfonic acid, and
    C. the D,L-aminocaprolactam diasereomeric salts of the acids L-pyrrolidonecarboxylic acid, D-N-carbamoylvaline, L-N-p-nitrobenzoylglutamic acid, L-N-benzoylglutamic acid, L-N-p-toluylglutamic acid and L-N-p-chlorobenzoylglutamic acid, to the desired isomer of said aminocaprolactam compound which comprises
    a. forming a supersaturated feed solution of said D,L-aminocaprolactam compound in an inert solvent; said solution also containing D,L-aminocaprolactam, and a strong base when said D,L-aminocaprolactam compound is a complex, and, when said D,L-aminocaprolactam compound is a salt or diastereomeric salt, a compound of the formula I or II

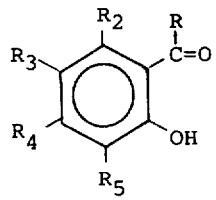
(I)

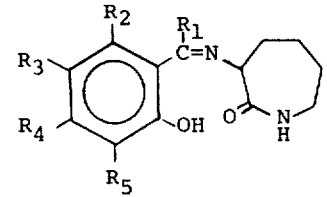
(II)

wherein $R_1$ is hydrogen or methyl and $R_2$ through $R_5$ are hydrogen, nitro, halogen, cyano or carboxylic substituents, and a metal ion selected from the group consisting of $Fe^{2+}$, $Fe^{3+}$, $Al^{3+}$, $Cu^{2+}$, $Co^{2+}$, $Zn^{2+}$ and $Ni^{2+}$, and maintaining said solution at a temperature of below 120°C.;

b. contacting said solution with seed crystals of the desired isomer of said aminocaprolactam compound, said contact being optional in the case that said aminocaprolactam compound is a diastereomeric salt; and c. removing the grown crystals of said compound.

2. The process of claim 1 which is continuous and wherein said feed solution is introduced continuously and wherein grown crystals and solvent which is introduced as a part of said feed solution are removed continuously.

3. The process of claim 2 wherein seed crystals of the desired isomer are fed continuously to maintain optical purity of the crystals grown from said supersaturated solution.

4. A method for the racemization of the D- or L-enantiomer of α-amino-ε-caprolactam comprising reacting the enantiomer with ions in the plus 2 valence state of nickel or cobalt, in a mol ratio ranging from at least 3.5:1 to about 20:1 in the presence of a catalytic amount of a strong base.

5. The process of claim 4 wherein the mol ratio of the enantiomer to the metal ion is within the range of about 3.5:1 to about 10:1.

6. The process of claim 4 wherein the salt forming metal complex is a member of the group consisting of nickel (II) chloride and cobalt (II) chloride.

7. The process of claim 4 wherein the strong base is present in an amount of 1–100 mol % based on the metal ion.

8. The process of claim 4 wherein 1 to 3 mol of a member of the group consisting of ethylene diamine, sodium lysinate, 1,10-phenanthroline and ammonia are added per mol of metal ion.

9. The process of claim 4 wherein the base is a hydroxide or alkoxide of the metal ion employed in the complex.

10. The process of claim 4 wherein the reaction temperature is in the range of about 40° to 95°C.

11. The process of claim 9 wherein the metal hydroxide or alkoxide is obtained by treating an alcoholic or aqueous alcoholic solution of the metal ion with a strongly basic or weakly basic ion exchange resin.

12. A single stage process for effecting transformation of D,L-aminocaprolactam to the desired enantiomer of aminocaprolactam comprising contacting in an inert solvent said D,L-aminocaprolactam with ions in the plus 2 valence state of nickel or cobalt, in a mole ratio ranging from at least 3.5:1 to about 20:1, a catalytic amount of a strong base, and seed crystals of a complex of the desired enantiomer of aminocaprolactam with ions in the plus 2 valence state of nickel or cobalt, and removing the grown crystals of said complex.

13. The process of claim 12 wherein the mol ratio of the aminocaprolactam to metal ion is within the range of about 3.5:1 to about 10:1.

14. A process for the optical purification of optically impure α-aminocaprolactam nickel complex or cobalt complex comprising partially dissolving said impure complex in an alcohol or water, or mixtures thereof, and recovering the remaining undissolved crystals in a state of substantially improved optical purity.

15. A continous process for effecting transformation of racemic α-amino-ε-caprolactam to the desired enantiomer of α-amino-ε-caprolactam comprising the steps of:

a. forming a supersaturated solution of the racemic material with a complex forming metal ion in the plus 2 valence state of nickel or cobalt in amounts such that the mol ratio of said racemic material to the metal ion in the solution is in the range from about 3.5:1 to about 10:1, said solution containing also a strong base in amounts from 1 to 100 mol % with respect to the metal ion;

b. contacting said solution with at least about 1% by weight preformed seeds of the desired enantiometer of said complex;

c. separating the crystalline product of the desired enantiomer complex from the reaction mother liquor;

d. partially dissolving the crystalline product from step (c) and recycling the remaining purified crystalline product as seed to step (b), decomposing the resulting solution at a temperature greater than about 0°C. by contacting it with a solution of a strong acid, and separating the resulting optically active α-amino-ε-caprolactam acid salt crystals from liquors containing primarily complex forming metal ions;

e. treating the liquors from (d) with an ion exchange resin to eliminate excess acid and introducing the treated liquors which contain complex forming metal ion to step (a).

16. An aminocaprolactam Schiff base of the formula

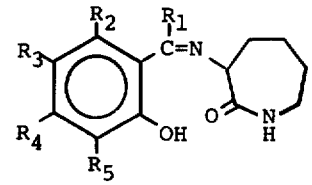

wherein $R_1$ is hydrogen or methyl and $R_2$ through $R_5$ are hydrogen, nitro, halogen, cyano or carboxylic substituents.

17. A complex selected from the group consisting of those formed by reacting the (a) Schiff bases of claim 16 and (b) metal salts of transition metals selected from the group consisting of $Fe''$, $Fe'''$, $Cu''$, $Zn''$, $Al'''$, $Ni''$ and $Co''$.

18. The composition of claim 17 wherein the transition metal is iron.

19. The process of claim 12 wherein the nickel ion is provided by nickel (II) chloride and the cobalt ion by cobalt (II) chloride.

20. The process of claim 15 wherein the nickel ion is provided by nickel (II) chloride and the cobalt ion by cobalt (II) chloride.

21. A method for the racemization of the D- or L-enantiomer of aminocaprolactam salts comprising reacting said salts in an inert solvent with D- or L-aminocaprolactam, a compound of formula I or II

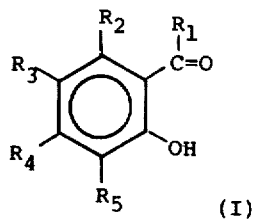
(I)
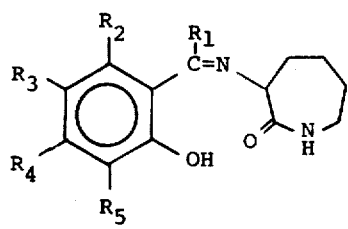
(II)
wherein $R_1$ is hydrogen or methyl and $R_2$ through $R_5$ are hydrogen, nitro, halogen, cyano or carboxylic substituents, and a metal ion selected from the group consisting of $Fe^{2+}$, $Fe^{3+}$, $Al^{3+}$, $Cu^{2+}$, $Co^{2+}$, $Zn^{2+}$ and $Ni^{2+}$ in a common inert solvent at the temperature range of 45° to 120°C.
* * * * *

UNITED STATES PATENT AND TRADEMARK OFFICE
CERTIFICATE OF CORRECTION

PATENT NO. : 3,941,776

DATED : March 2, 1976

INVENTOR(S) : Stylianos Sifniades, William J. Boyle, Jr. and Jan F. Van Peppen

It is certified that error appears in the above-identified patent and that said Letters Patent are hereby corrected as shown below:

Column 6, line 33, "$C_D\ 2C_L$" should be -- $C_D \leq 2C_L$ --.

Column 8, line 33, "pressure" should be -- presence --.

line 42, "ethoside" should be -- ethoxide --.

Column 9, line 9, "amincaprolactam" should be -- aminocaprolactam --.

line 31, "recrystallization" should be -- crystallization --.

Column 10, line 61, the formula "L-α-ACL.NI" should read -- L-α-ACL·Ni --.

Column 11, line 1, "now" should be -- not --.

line 24, "enantiometer" should be -- enantiomer --.

Column 12, between first two ring compounds, insert plus sign (+) as shown:

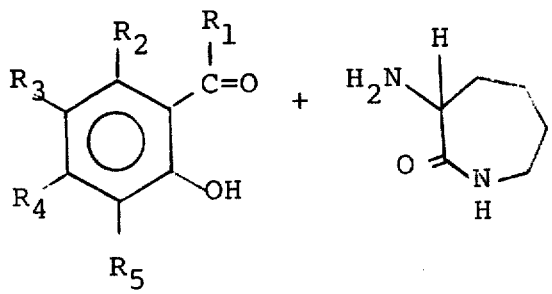

UNITED STATES PATENT AND TRADEMARK OFFICE
CERTIFICATE OF CORRECTION

PATENT NO. : 3,941,776
DATED : March 2, 1976
INVENTOR(S) : Stylianos Sifniades, William J. Boyle, Jr. and Jan F. Van Peppen It is certified that error appears in the above-identified patent and that said Letters Patent are hereby corrected as shown below:

Column 14, line 3, after the word "room" insert -- temperature --.

Column 16, line 17, "$Cl^+$" should be -- $Cl^-$ --.

Column 17, line 10, "Yiled" should be -- Yield --.

line 29, "KCL" should be -- KCl --.

line 43, "$ACL)_2NiCl_2$" should be -- $ACL)_3NiCl_2$ --.

line 58, "mml" should be -- mmol --.

Column 18, line 1, "0.717" should be -- 7.7 --.

line 6, "optial" should be -- optical --.

line 54, "$NicL_2.H_2O$" should be -- $NiCl_2 \cdot H_2O$ --.

Column 21, line 52, "mols" should be -- mmols --.

Column 24, claim 1, in formula (I), that portion of the formula

Column 26, claim 15, under (b), "enantiometer" should be -- enantiomer --.

claim 18, "metai" should be -- metal --.

Signed and Sealed this

Tenth Day of August 1976

[SEAL]

Attest:

RUTH C. MASON
Attesting Officer

C. MARSHALL DANN
Commissioner of Patents and Trademarks